(12) United States Patent
Kim

(10) Patent No.: US 6,604,529 B2
(45) Date of Patent: Aug. 12, 2003

(54) EXTERNAL ELECTROMAGNETIC SYSTEM FOR ASSISTING SYSTOLIC AND DIASTOLIC VENTRICULAR FUNCTION, AND METHOD THEREFOR

(76) Inventor: Young D. Kim, 1008 Gelston Cir., McLean, VA (US) 22102

(*) Notice: Subject to any disclaimer, the term of this patent is extended or adjusted under 35 U.S.C. 154(b) by 0 days.

(21) Appl. No.: 10/170,625

(22) Filed: Jun. 14, 2002

(65) Prior Publication Data
US 2002/0156339 A1 Oct. 24, 2002

Related U.S. Application Data

(63) Continuation-in-part of application No. PCT/US02/12703, filed on Apr. 23, 2002.
(60) Provisional application No. 60/285,707, filed on Apr. 24, 2001.

(51) Int. Cl.[7] .................................................. A61M 1/12
(52) U.S. Cl. .......................... 128/899; 600/17; 600/16
(58) Field of Search .................. 128/899; 600/9–18, 600/373, 375; 607/126–128

(56) References Cited

U.S. PATENT DOCUMENTS

| 4,621,617 A | 11/1986 | Sharma |
| 4,913,164 A | 4/1990 | Greene et al. |
| 5,498,228 A | 3/1996 | Royalty et al. |
| 6,099,460 A | 8/2000 | Denker |
| 6,123,724 A | 9/2000 | Denker |

*Primary Examiner*—Samuel G. Gilbert
(74) *Attorney, Agent, or Firm*—Foley & Lardner

(57) ABSTRACT

A method of aiding the compression and relaxation of a heart chamber using ferromagnetic and diamagnetic pellets inserted into the anterior and posterior walls of the chamber is provided. The pellets are inserted into the myocardial walls of the heart chamber by means of a delivery catheter. Electromagnetic fields, which are used to push and pull the pellets to compress and relax the hear chamber, are cyclically generated by electromagnetic field generators positioned on a patient's chest and back wall.

8 Claims, 3 Drawing Sheets

_EXTERNAL ELECTROMAGNETIC SYSTEM FOR ASSISTING SYSTOLIC AND DIASTOLIC VENTRICULAR FUNCTION, AND METHOD THEREFOR_

CROSS REFERENCE TO RELATED APPLICATIONS

This application is a continuation-in-part of PCT Patent Application Serial No. PCT/US02/12703 filed on Apr. 23, 2002 which claimed priority to U.S. Provisional Application No. 60/285,707 filed on Apr. 24, 2001.

BACKGROUND OF THE INVENTION

1. Field of the Invention

The present invention relates to the field of artificially assisting heart function. More particularly, the invention relates to a device and a method for electromagnetically assisting the function of the ventricles in the heart.

2. Description of the Related Art

Despite the significant progress in prevention and medical treatment of cardiovascular disease, congestive heart failure (CHF) affects about 1 percent of adults in the United States (i.e. approximately 4–5 million patients), with 400,000 new cases occurring each year. CHF is the primary diagnosis for about 1 million hospitalizations each year and is a contributing factor in over 250,000 deaths annually. The age-adjusted death rate from CHF is 106.4 per 100,000. The median survival, after diagnosis, is 1.7 years for men and 3.2 years for women; the five year survival rate is less than 50 percent. It is estimated that nearly 60,000 patients annually in the United States could benefit from heart transplantation or long-term mechanical support. Evaluation and care of CHF patients costs our society in excess of $11 billion each year.

Currently, heart transplantation is considered the most effective therapy for end-stage CHF. However, heart transplantation presents multiple problems, including: (1) a shortage of donor hearts; (2) a significant perioperative morbidity/mortality rate; (3) the requirement of immune suppression; and (4) a less than ideal long-term survival rate. Accordingly, there is a crucial need for the development of alternatives to heart transplantation.

Mechanical support by means of implantable ventricular assist devices presently is the most promising alternative to heart transplantation. Currently available assist devices include extracorporeal oxygenators, univentricular and biventricular extracorporeal devices, and total artificial hearts. Most of these devices require the patients to be connected to cumbersome drive systems which makes their use limited only to hospital in-patients.

Lately, the development of an implantable left ventricular assist device (LVAD) and the development of wearable power supplies for this device has made the following possible: (1) a patient's rehabilitation; (2) unrestricted patient mobility; (3) patient discharge to the home; and (4) a patient's ability to return to work. However, while an LVAD may have some advantages over heart transplantation, an LVAD still presents many serious limitations for long-term use. These limitations include: (1) selection of patients (i.e., an LVAD is only available to patients without end-organ failure and qualification for an LVAD is as restricted as heart transplantation); (2) an LVAD is unavailable for patients on long-term glucocorticoid therapy or patients with a small body surface area; (3) it is difficult to assess a patient's ability to manage an LVAD; (4) early post-operative complications such as bleeding, right heart failure, air embolism, and multiple organ failure are possible; and (5) late post-operative complications such as infection, thromboembolism. In addition, most LVADs are designed to assist systolic pumping ability only whereas impairment of diastolic relaxation ability is a major component of CHF.

For these and other reasons, a new device is needed which can assist systolic and diatolic function of the ventricles, which is available to a wide variety of patients, and which does not cause at least some of the early and late post-operative complications previously mentioned.

SUMMARY OF THE INVENTION

A virtual ventricular assist device (VVAD), herein disclosed, is designed to overcome many of the aforementioned limitations of an LVAD. For long-term use, the VVAD: (1) can assist systolic pumping and diastolic relaxation of CHF patients without structural defects (i.e., congenital or acquired valvular diseases); (2) requires no major surgery to implant and, therefore, avoids the early complications mentioned above; (3) requires no foreign materials to interact with the surface of the ventricular cavity or conduit vessels and, therefore, avoids the late complications mentioned above; (4) can be used for the right as well as the left ventricle; and (5) eliminates the need for anticoagulants.

The VVAD consists of essentially two components: (a) implantable magnetic pellets implanted through a delivery catheter; and (b) an external electromagnetic device which, when cyclically charged, attracts or repels the pellets depending on their corresponding charge. The term "pellet" is not to be limited to ball shaped materials; it is to be construed to include many other shapes including that of a plate or umbrella. Moreover, the pellets are "magnetic" in the sense that they react to magnetic fields in a manner similar to metals due to the presence of free electrons which orient themselves in response to a magnetic field; the pellets themselves are not charged.

The implantable pellets are spring-winged, contain materials which are responsive to magnetic fields, and are vacuum-sealed within a polyurethane membrane (or any other biologically inert, synthetic material). The pellets have a myocardial wall contact portion to which a plurality of wings is hingedly connected. Preferably, the pellets are deployed percutaneously to the mid-layer of the targeted myocardial wall through a major artery using a delivery catheter. It is also possible to implant the pellets through the chest wall and into a mid-layer of the targeted myocardium; this transthoracic implantation requires a minimally invasive surgical procedure using a thoracic endoscope. It is also possible to fix the pellets to the outside of the myocardial wall. Pellets made of diamagnetic metals (e.g., bismuth or antimony) are implanted in or on the posterior wall of the left ventricle (LV) whereas pellets made of ferromagnetic metals (e.g., iron or cobalt) are implanted in or on the anterior wall of the left ventricle. The shape of the pellet will depend on the location in which they are fixed and by the method by which they are introduced into the ventricle. For example, in a transthoracic approach, the implantable magnetic pellets can be plate shaped or umbrella shaped like a shell so that they can be implanted on the surface of the targeted myocardium.

The external electromagnetic device (which is battery operated and light enough to be worn in the chest wall) generates an electromagnetic force which is synchronized with an EKG, at least one lead of which monitors the user's heart rate. This electromagnetic device may be external or internal to the chest wall. Onset of the force corresponds to the EKG's R wave whereas offset of the force corresponds to the EKG's T wave. Due to the charge of the electromagnetic field, pellets implanted in the posterior wall of the left ventricle will be pulled toward the electromagnetic device while the pellets in the anterior wall of the left ventricle will be correspondingly pushed away from the electromagnetic device. Due to this opposite motion, a compression of the left ventricle occurs. When the electromagnetic field is discontinued (due to the occurrence of the EKG T wave), the anterior and posterior walls of the left ventricle (which hold the magnetic pellets) return to their original positions. In this fashion, a cyclical compression of the left ventricle occurs thereby allowing the left ventricle to beat as if it were normal and healthy. This synchronized generation of electromagnetic force is designed to boost systolic pumping only during the early half of systole. Moreover, the magnitude of the electromagnetic force generated and its domain are adjusted to boost systolic function by 10–20 percent.

Pellets are implanted into the myocardium after being introduced into the body via a delivery catheter. The delivery catheter contains a mobile electromagnetic rod which is approximately 7 mm in length. The delivery catheter (preferably size 7 FOD, 120 cm) can be introduced into the body by means of a introducer catheter set which can be any commercially available percutaneous introducer set of size 8 F. If the delivery catheter can be introduced percutaneoulsy through a femoral artery, it is guided into the left ventricle by an external magnetic system working in conjunction with a fluorscope. In the alternative, the delivery catheter can be introduced through a transthoracic-epicardial route; this is a video-assisted method in which the pellets are implanted trans-epicardially into the targeted myocardium.

A spring-winged pellet is attached to the distal end of the electromagnetic rod. A wire (within the catheter) connects the proximal end of rod to an electromagnetic power generator and thereby supplies current to the rod; the current charges the electromagnetic rod thereby creating an electromagnetic field around the rod. The electromagnetic field causes the wings of the spring-winged pellet to overcome their otherwise extended orientation and thereby to collapse on the electromagnetic rod. The pellet is maintained in this fashion until it is positioned within the myocardium. When the pellet (attached to the catheter tip) is positioned against the targeted myocardial wall position, the catheter tip is forcefully anchored against the endo-myocardial wall by an external magnet. An injection syringe then hydraulically forces the rod with the pellet into the myocardium. When the pellet is placed within the myocardium, the current supplied to the electromagnetic rod via the wire is discontinued causing the wings to open thereby preventing the pellet from travelling backwards (i.e., in the direction of the delivery catheter when the catheter is removed). After the wings have opened, the rod is hydraulically pulled back into the catheter which is then removed from the body.

In this fashion, pellets should be deployed one at a time. In addition, 3 or 4 pellets (or as many as needed) should be positioned in each ventricular myocardial wall (i.e., anterior and posterior) and should be distributed to cover 6–15 square cm of myocardial area.

The present invention includes a novel magnetic spring-winged pellet, a method of inserting the pellet, and a method of treating congestive heart failure using spring-winged pellets implanted in or on the myocardial walls of a ventricle in conjunction with an external electromagnetic field generator.

One embodiment of the spring-winged pellet includes: (a) a contact portion; and (b) a plurality of wings. In this embodiment each wing has a distal end portion hingedly connected to the contact portion and each wing has a proximal end portion which bends toward the proximal end portions of the other wings when an electromagnetic field is applied to the pellet.

One method of inserting a magnetic pellet into a myocardial wall of a heart includes: (a) supplying an electromagnetic field to the pellet which has a plurality of spring-wings and which is attached to a distal end of an electromagnetic rod which is positioned within a delivery catheter; (b) positioning the magnetic pellet at a target area on the myocardial wall; (c) using an injection syringe positioned at a proximal end of the catheter to force the pellet into the myocardial wall; and (d) removing the electromagnetic field previously supplied to the pellet and thereby causing the spring-wings to open. Preferably, the myocardial wall into which the pellets are inserted is in the heart's left ventricle. Moreover, the wall can be either a posterior wall or an anterior wall of the left ventricle. However, the pellets may also be inserted into the myocardial wall of the right ventricle wall using a transthoracic insertion. The electromagnetic field is preferably created by external electromagnetic generator which is electrically connected to a proximal end of the electromagnetic rod by a wire. Finally, this method can be practiced by introducing the delivery catheter to the target area of the myocardial wall by sending the catheter through a femoral artery or by transthoracically sending the catheter through a chest wall.

A preferred method of treating a patient's congestive heart failure includes: (a) positioning a first plurality of magnetic spring-winged pellets in a myocardium of posterior wall of a ventricle of a heart; (b) positioning a second plurality of magnetic spring-winged pellets in a myocardium of an anterior wall of a ventricle of a heart; (c) using an electromagnetic generator to cyclically generate an electromagnetic field which magnetically interacts with the first and the second plurality of pellets; (d) magnetically pulling, in response to the cyclical electromagnetic field, the first plurality of pellets toward the electromagnetic generator; and (e) magnetically pushing, in response to the cyclical electromagnetic field, the second plurality of pellets away from the electromagnetic generator. Ideally, this method also includes: (f) positioning an EKG monitor on the patient and generating a waveform of the heart's electrical activity; and (g) synchronizing the cyclical electromagnetic field to correspond to the heart's electrical activity.

A method is also provided to aid in the compression and relaxation of a heart chamber (which may be the heart's left ventricle) of a patient. This method includes: (a) inserting a plurality of ferromagnetic pellets into the anterior wall of the heart chamber and inserting a plurality of diamagnetic pellets into the posterior wall of the heart chamber; (b) positioning a first electromagnetic field generator on the chest wall of the patient and a second electromagnetic field generator on the back wall of the patient; (c) generating a first electromagnetic field with the first electromagnetic field generator thereby pushing the ferromagnetic pellets in the anterior wall away from the first electromagnetic field generator and pulling the diamagnetic pellets in the posterior wall toward the first electromagnetic field generator to compress the heart chamber; (d) discontinuing the first electromagnetic field generated by the first electromagnetic field generator; (e) generating a second electromagnetic field with the second electromagnetic field generator thereby pulling the diamagnetic pellets in the posterior wall toward the second electromagnetic field generator and pushing the ferromagnetic pellets in the anterior wall away from the second electromagnetic field generator to relax the heart chamber; and (f) discontinuing the second electromagnetic field generated by the second electromagnetic field generator. The steps of creating the electromagnetic fields to compress and relax the heart chamber are then cyclically repeated. In addition, this method may also include: (g) positioning an EKG monitor on the patient and generating a waveform of the heart's electrical activity; and (h) synchronizing the cyclical electromagnetic fields generated by the first and second electromagnetic field generators to correspond to the heart's electrical activity. This method can also be performed by placing the ferromagnetic pellets in the posterior wall and the diamagnetic pellets in the anterior wall, provided, however, that the electromagnetic field generators are corresponding switched.

These and other features, aspects, and advantages of the present invention will become more apparent from the following description, appended claims, and accompanying exemplary embodiments shown in the drawings.

BRIEF DESCRIPTION OF THE DRAWINGS

The accompanying drawings, which are incorporated in and constitute a part of the specification, illustrate an embodiment of the invention and together with the description, serve to explain the principles of the invention.

DETAILED DESCRIPTION OF THE PREFERRED EMBODIMENT

Figure 2A:
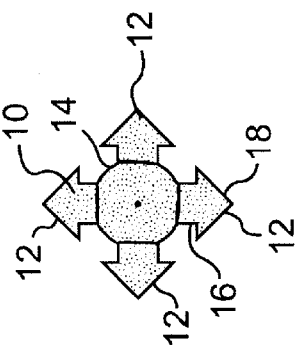
FIG. 2a is an end view of a magnetic pellet showing the spring-wings in a collapsed orientation.
Figure 1A:
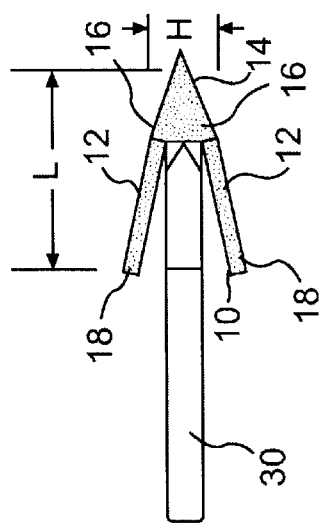
FIG. 1a is a longitudinal view of an electromagnetic rod to which a pellet is attached such that the spring-wings are collapsed on the sides of the rod.
Figure 2B:
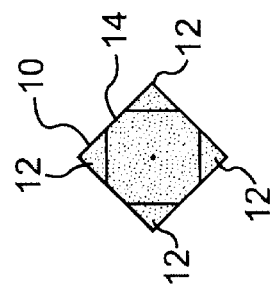
FIG. 2b is an end view of a discharged pellet showing the spring-wings in an open orientation.
Figure 1B:
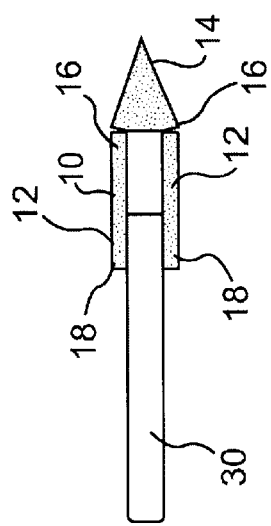
FIG. 1b is a longitudinal view of the electromagnetic rod of FIG. 1a in which the electromagnetic field supplied to the pellet has been removed causing the spring-wings to open.
Figure 3:
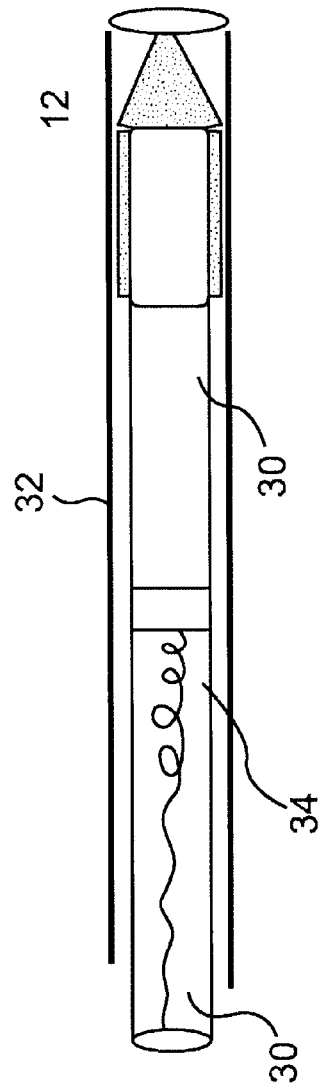
FIG. 3 is a longitudinal view of a delivery catheter containing an electromagnetic rod to which a pellet is attached.
Figure 4:
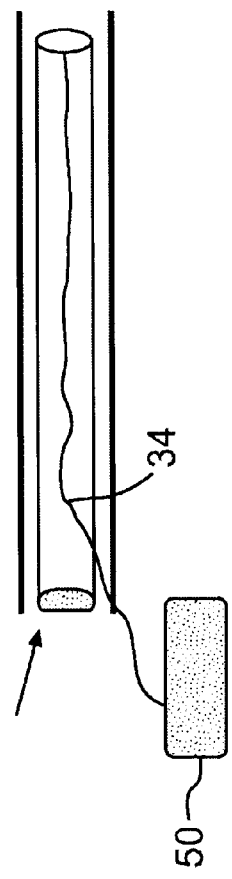
FIG. 4 is a longitudinal view of the delivery catheter of FIG. 3 in which an injection syringe is positioned at a proximal end of the catheter.

Reference will now be made in detail to a presently preferred embodiment of the invention, which is illustrated in the drawings. An effort has been made to use the same reference numbers throughout the drawings to refer to the same or like parts.

FIGS. 1A–2B detail an electromagnetic pellet 10 which is inserted into a left ventricle 20 (shown in FIG. 5) of a patient. The pellets 10 react to magnetic fields in a manner similar to metals due to the presence of free electrons which orient themselves in response to a magnetic field; the pellets 10 themselves are not charged. The structure of the two sets of pellets 10 will be described herein will be identical; the only difference is that one of the sets of pellets 10 are diamagnetic (e.g., bismuth or antimony) and the other set of pellets 10 is ferromagnetic (e.g., iron or cobalt).

The pellet 10 is formed of a plurality of wings 12 and a sharp pointed contact portion 14. For reasons which will hereafter be described in detail, the pellet 10 has two configurations: a closed configuration (FIGS. 1A, 2A) in which the wings 12 approach each other; and an open configuration (FIGS. 1B, 2B) in which the wings 12 project away from each other.

Although the pellet 10 has at least two wings 12, it is preferable to have at least four wings 12. Each of the wings 12 has a distal end 16 and a proximal 18. The distal ends 16 of the wings 12 are hingedly attached to the contact portion 14 of the pellet 10. The proximal 18 is preferably blunt so that the plurality of wings 12 may act as a barb when the pellet 10 is in the open configuration.

The wings 18 are biased toward the open configuration, such bias can be achieved according to a number of conventional mechanisms including a living hinge, being spring loaded, etc. However, it is preferable that the wings 12 be biased by a living hinge. This bias, however, can be overcome as later explained. When in the closed position, the pellet 10 has a height H of approximately 1.5 mm. In the open position, however, the pellet 10 has a height of approximately 4.0–5.0 mm.

The pellets 10 are introduced into a patient by being carried on an electromagnetic rod 30 which is about 7 mm long. A conductive wire 34 is connected, on one end, to the electromagnetic rod 30 and at the other end, to an electromagnetic power source 50. To connect the pellet 10 to the electromagnetic rod 30, a pellet 10 in the open position is placed on the end of the rod 30. At this time, current is sent via the wire 34 to the electromagnetic rod 30 thereby charging the rod 30. Assuming the pellets 10 are ferromagnetic, the rod 30 will be charged so that it emits an electromagnetic field that will attract the wings 12 of the ferromagnetic pellets 10. In response to the electromagnetic field emitted by the rod 30, the ferromagnetic wings 12 are magnetically drawn onto the sides of the rod thereby placing the pellet 10 in the closed configuration. The rod 30, with the 10 pellet attached thereto, is then journalled into a catheter 32. The catheter 32, with the rod 30 and pellet 10 therein, is then directed, via a femoral artery such as the aorta 22, to a chamber of a heart 24 of a patient. Although the chamber discussed in detail herein is the left ventricle 20, the procedure is equally applicable to the right ventricle. Further, it is also possible to direct the catheter to the ventricles transthoracically, i.e., sending the catheter through the patient's chest wall 26, rather than through a femoral artery.

When in the left ventricle 20, the ferromagnetic pellet 10 is placed adjacent the anterior wall 25 of the left ventricle 20. The pellet is firmly held in position against the endo-cardial wall 25 by an external magnet positioned outside of the patient's chest wall 26. The sharp contact portion 14 of the pellet 10 is then forced into the myocardium of the anterior wall 25 by an injection syringe which hydraulically forces the rod 30 with the pellet 10 attached thereto into the myocardium of the wall 25. The pellet 10 is inserted so that the contact portion 14 is about 10 mm into the wall 25. As the pellet 10, when in the open configuration has a length L of about 5 mm high, the pellet 10 will be completely submerged in the anterior wall 25 to a depth of approximately 5 mm.

The current sent to the electromagnetic rod 30 is then discontinued thereby removing the charge originally added to the rod 30. As a result of the loss in charge in the rod 30, the wings 12 of the pellet 10 will return to their biased open configuration. As the proximal ends 18 of the wings 12 are blunt and will, therefore, not easily cut through the tissue of the anterior wall 25, the wings 12 of the pellet 10 will act as a barb maintaining the ferromagnetic pellet 10 in the anterior wall 25. This process is repeated until a sufficient number of ferromagnetic pellets 10 are implanted in the anterior wall 25 of the left ventricle 20. Preferably, at least three or four ferromagnetic pellets 10 will be implanted in the anterior wall 25 and are distributed over an area of about 6–15 cm$^2$.

After the ferromagnetic pellets 10 are inserted in the anterior wall 25, a similar number of diamagnetic pellets 10 are inserted, using the same technique, in the posterior wall 27. However, in inserting the diamagnetic pellets 10 into the posterior wall 27, the polarity of the electromagnetic rod 30 must be reversed so that it will be adapted to force the diamagnetic pellets 10 into the closed configuration.

After the pellets 10 are inserted in the anterior wall 25 and the posterior wall 27, the catheter 32 is removed from the patient. At this time an electromagnetic generator 40 can be placed on the patient's chest wall 26. By cyclically generating an electromagnetic field with the electromagnetic generator 40, the pellets 10 in the anterior wall 25 will be pushed away from the electromagnetic generator 40 while the pellets 10 in the posterior chest wall 27 will be pulled toward the electromagnetic generator 40. As the pellets 10 in the anterior wall 25 and the posterior wall 27 approach each other, the result is an artificially assisted contraction of the left ventricle 20.

Figure 5:
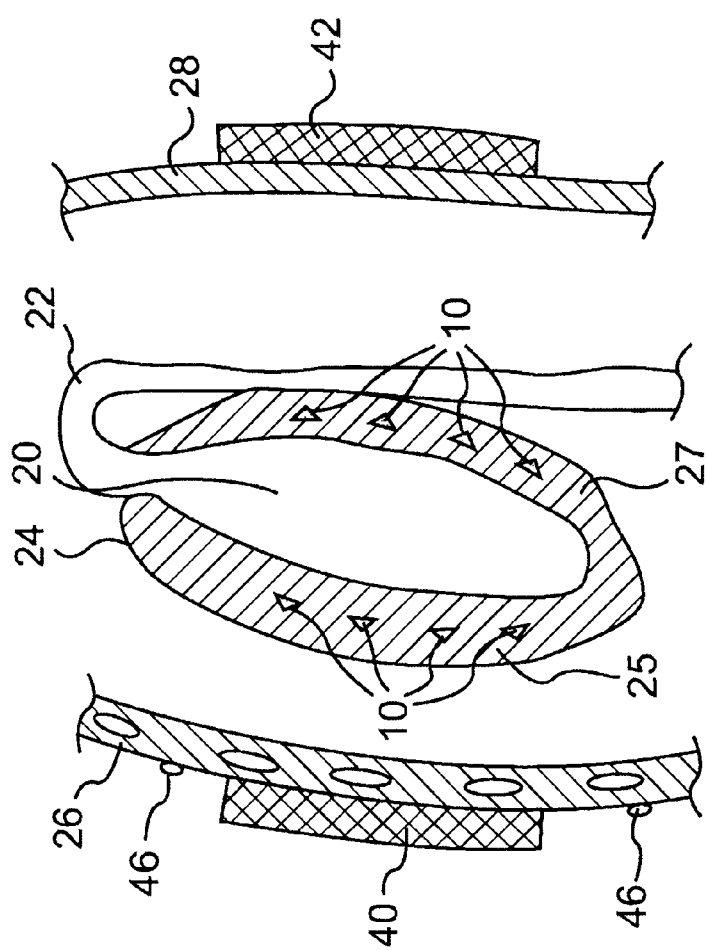
FIG. 5 is a cross-sectional view of a left ventricle of a heart in which magnetic pellets have been placed in the anterior and posterior myocardial walls.

It is also possible to place a second electromagnetic generator 42 on the patient's back wall to aid the ventricle in relaxing between compressions, as shown in FIG. 5. The second generator 42 preferably would cyclically generate an electromagnetic field which is out of phase with the electromagnetic field generated by the first generator 40. With the second electromagnetic generator, the following would occur in succession: (a) the first generator 40 generates an electromagnetic field which will push the ferromagnetic pellets 10 in the anterior wall 25 away from the first generator 40 while simultaneously pulling the diamagnetic pellets 10 in the posterior wall 27 toward the first generator 40 thereby compressing the ventricle; (b) the electromagnetic field generated by the first generator 40 is discontinued; (c) the second generator 42 generates an electromagnetic field which will pull the pellets 10 in the posterior wall 27 toward the second generator 42 while simultaneously pushing the pellets 10 in the anterior wall 25 away from the second generator 42 thereby relaxing the ventricle; (c) the electromagnetic field generated by the second generator 42 is discontinued; and (d) steps (a) through (c) are repeated.

The electrical activity in the heart 24, generated in response to the contraction of the left ventricle 20, can be monitored with a conventional EKG monitor (not shown) having leads 46 attached to the patient's chest wall 26. Further, the EKG can output a waveform representative of the electrical activity which a doctor can interpret to determine whether the heart 24 is functioning appropriately. Finally, the cyclical electromagnetic fields generated by the electromagnetic generators 40, 42 can be adjusted in response to the output of the EKG. The adjustment may be manual and/or automatic, if the EKG and the electromagnetic generator 40 are connected to a computer.

If the two electromagnetic generators 40, 42 are employed in conjunction with an EKG, it is preferable that the electromagnetic generator 40 on the chest wall 26 generate an electromagnetic field in sync with the onset of the "R" portion of the EKG "QRS" wave and the offset of the EKG "T" wave. Similarly, the electromagnetic generator 42 on the back wall 28 will generate an electromagnetic field in sync with the onset of the EKG "T" wave and the offset of the EKG "QRS" wave. The magnitude of the force and domain of the electromagnetic fields may be adjusted to boost the ejection fraction of the ventricle (or other heart chamber) by 10–20%.

Although the aforementioned describes preferred embodiments of the invention, the invention is not so restricted. It will be apparent to those skilled in the art that various modifications and variations can be made to the disclosed preferred embodiments of the present invention without departing from the scope or spirit of the invention. For example, although not preferable, it is possible to use one type of pellet (diamagnetic or ferromagnetic) 10 implanted in both the anterior wall 25 and the posterior wall 27. However, this approach will require a second electromagnetic generator 40, emitting the same cyclical electromagnetic field as the electromagnetic generator on the chest wall 26, to be placed on the patient's back wall 28. Both electromagnetic generators 40 would then push the pellets 10 in the anterior wall 25 toward the pellets 10 in the posterior wall 27. This method would not be preferred not because it uses two generators 40 but also because the pellets 10 in the ventricle may react to both generators thereby tending to remain stationary.

Accordingly, it should be understood that the apparatus and method described herein are illustrative only and are not limiting upon the scope of the invention, which is indicated by the following claims. Accordingly, alternatives which would be obvious to one of ordinary skill in the art upon reading the teachings herein disclosed, are hereby within the scope of this invention.

What is claimed is:

1. A method of compressing and relaxing a chamber in a heart of a patient comprising the steps of:
   (a) inserting a plurality of ferromagnetic pellets into the anterior wall of the heart chamber;
   (b) inserting a plurality of diamagnetic pellets into the posterior wall of the heart chamber;
   (c) positioning a first electromagnetic field generator on a chest wall of the patient;
   (d) positioning a second electromagnetic field generator on a back wall of the patient;
   (e) generating a first electromagnetic field with the first electromagnetic field generator thereby pushing the ferromagnetic pellets in the anterior wall away from the first electromagnetic field generator and pulling the diamagnetic pellets in the posterior wall toward the first electromagnetic field generator to compress the heart chamber;
   (f) discontinuing the first electromagnetic field generated by the first electromagnetic field generator;
   (g) generating a second electromagnetic field with the second electromagnetic field generator thereby pulling the diamagnetic pellets in the posterior wall toward the second electromagnetic field generator and pushing the ferromagnetic pellets in the anterior wall away from the second electromagnetic field generator to relax the heart chamber;
   (h) discontinuing the second electromagnetic field generated by the second electromagnetic field generator; and
   (i) repeating cyclically steps (e)–(h).

2. The method of claim 1, wherein the heart chamber is the heart's left ventricle.

3. The method of claim 1, wherein the pellets are inserted into the myocardium of the anterior and posterior walls.

4. The method of claim 1, further comprising the steps of:

(j) positioning an EKG monitor on the patient and generating a waveform of the heart's electrical activity; and (k) synchronizing the cyclical electromagnetic fields generated by the first and second electromagnetic field generators to correspond to the heart's electrical activity.

5. A method of compressing and relaxing a chamber in a heart of a patient comprising the steps of:

(a) inserting a plurality of diamagnetic pellets into the anterior wall of the heart chamber;

(b) inserting a plurality of ferromagnetic pellets into the posterior wall of the heart chamber;

(c) positioning a first electromagnetic field generator on a chest wall of the patient;

(d) positioning a second electromagnetic field generator on a back wall of the patient;

(e) generating a first electromagnetic field with the first electromagnetic field generator thereby pushing the diamagnetic pellets in the anterior wall away from the first electromagnetic field generator and pulling the ferromagnetic pellets in the posterior wall toward the first electromagnetic field generator to compress the heart chamber;

(f) discontinuing the first electromagnetic field generated by the first electromagnetic field generator;

(g) generating a second electromagnetic field with the second electromagnetic field generator thereby pulling the ferromagnetic pellets in the posterior wall toward the second electromagnetic field generator and pushing the diamagnetic pellets in the anterior wall away from the second electromagnetic field generator to relax the heart chamber;

(h) discontinuing the second electromagnetic field generated by the second electromagnetic field generator; and (i) repeating cyclically steps (e)–(h).

6. The method of claim 5, wherein the heart chamber is the heart's left ventricle.

7. The method of claim 5, wherein the pellets are inserted into the myocardium of the anterior and posterior walls.

8. The method of claim 5, further comprising the steps of:

(j) positioning an EKG monitor on the patient and generating a waveform of the heart's electrical activity; and (k) synchronizing the cyclical electromagnetic fields generated by the first and second electromagnetic field generators to correspond to the heart's electrical activity.

* * * * *